United States Patent [19]

Lamb et al.

[11] 4,413,360

[45] Nov. 8, 1983

[54] ADJUSTABLE PROSTHETIC ANKLE ASSEMBLY

[76] Inventors: Steve R. Lamb, 2772 Sydney Way, Castro Valley, Calif. 94546; Larry W. Lamoreux, 5470 Manila Ave., Oakland, Calif. 94618

[21] Appl. No.: 315,423

[22] Filed: Oct. 27, 1981

[51] Int. Cl.³ ............................................... A61F 1/04
[52] U.S. Cl. ................................................... 3/30; 3/5
[58] Field of Search ........................................ 3/30–35, 3/21, 7, 6, 2

[56] References Cited

U.S. PATENT DOCUMENTS 3,874,004 4/1975 May ............................................ 3/33
3,982,278 9/1976 May ........................................ 3/30 X

Primary Examiner—Richard J. Apley
Assistant Examiner—David J. Isabelle
Attorney, Agent, or Firm—Richard Esty Peterson

[57] ABSTRACT

An adjustable prosthetic ankle assembly for allowing the heel height of a prosthetic foot to be adjusted and secured in a position that is of optimum comfort and facility to the user, the ankle assembly has a mechanism interposed between an ankle block and a connected foot block with a pivot and associated adjustment screw for altering the fore and aft tilt of the foot block with respect to the ankle block.

7 Claims, 3 Drawing Figures

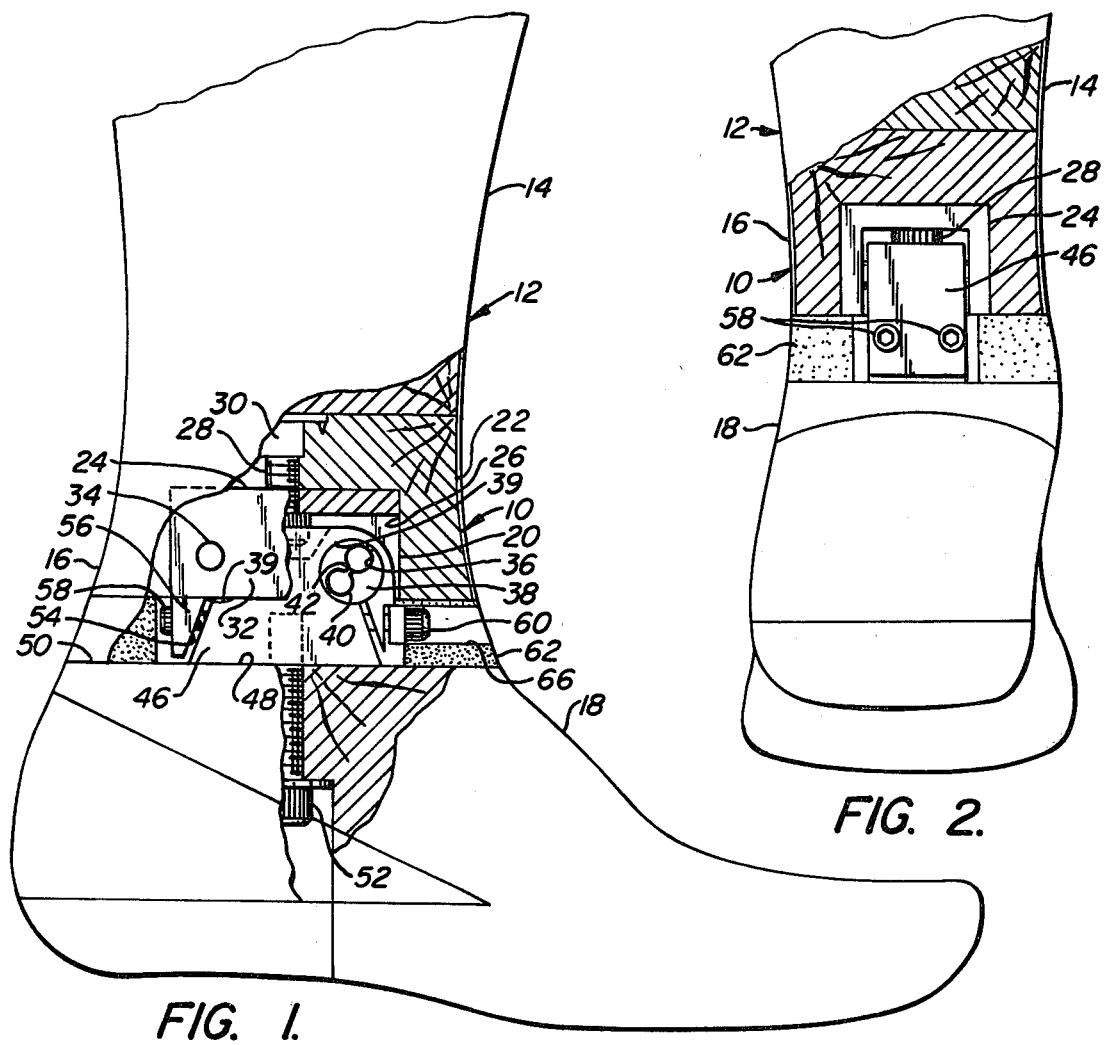
FIG. 1.
FIG. 2.
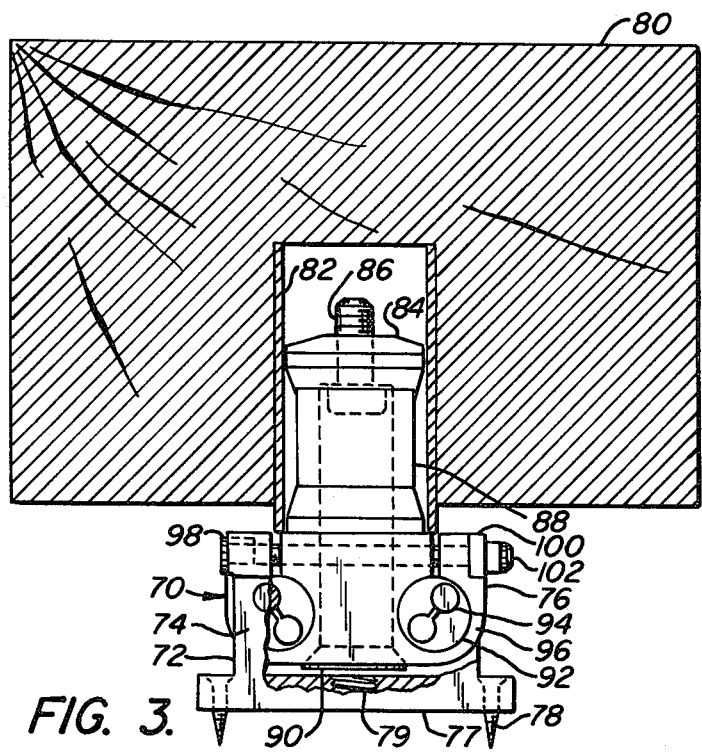
FIG. 3.

ADJUSTABLE PROSTHETIC ANKLE ASSEMBLY

BACKGROUND OF THE INVENTION

This invention relates to prosthetic devices and in particular to a foot prosthesis for amputees. The lower extremity of prosthetic devices for both below-knee and above-knee amputees is conventionally rigid with minor added cushioning particularly at the heel to allow the amputee a relatively firm control over the foot while walking.

Because the dynamic forces on the prosthetic leg and foot device are severe, the sculptured foot member is securely fixed to the leg member to form a rigid integral structure. Customarily, the amputee participates in the alignment and adjustment of the foot block prior to final shaping and bonding to the leg or ankle block. The resulting structure integrated leg is a laminated member that is permanently fixed to prevent subsequent misalignment. The initial alignment and adjustment fixes the heel height to a particular shoe and the user must continue to wear shoes that have identical heel heights. This often requires the amputee to wear the same model shoe, always. If a different shoe is worn, the stability of the prosthesis is affected, resulting in unnatural gait, and in some cases, an unsafe limb. While the leg member can be subsequently severed, realigned and adjusted for a different heel height, and again laminated, the user is again limited to a fixed prosthetic member.

The advantage of a prosthetic leg having a foot member with an adjustable heel height can be readily appreciated. The user can manually adjust the heel height of the foot member to the optimum position for comfort and safety for the particular shoes that he is wearing. This adjustment capability allows the amputee, with minor training, to self-adjust for any heel height he chooses. He is then afforded a wide variety of shoes, from heelless slippers to high heel boots.

A principal obstacle to a leg prosthesis with an adjustable heel is the tremendous dynamic forces applied to the prosthetic structure during even the simple act of walking. Further, because no wobble or misalignment can be tolerated, for obvious reasons of balance and safety, an adjustment mechanism must be strong and free from any problems of wear or loosening that would affect stability. Yet, the mechanism must be sufficiently compact to be concealed within the leg member. The adjustable prosthetic ankle assembly of this invention solves these problems and incorporates a safe adjustment mechanism into a leg prosthesis. The invented adjustable prosthetic ankle assembly provides a reliable and comfortable alternative to the fixed structure of the conventional device.

SUMMARY OF THE INVENTION

The adjustable prosthetic ankle assembly of this invention comprises a user adjustable mechanism located in the ankle section of a leg prosthesis for selective adjustment of the heel height. The adjustment capability allows the amputee user to adjust his leg prosthesis to permit the user to both adjust the heel height for safety and comfort for a particular shoe during initial fitting and to subsequently wear a variety of shoes of different heel heights eliminating his previous restriction to shoes of identical heel heights.

The adjustment mechanism is designed for incorporation into essentially all conventional leg prostheses for both above and below the knee leg amputees with only minor alterations in existing prosthetic leg structures.

The adjustment mechanism utilizes a double eccentric pivot and clamping means to provide a fore and aft pivot at the ankle section to effect an adjustment of the heel height while maintaining the overall structural integrity of the leg prosthesis. The particular mechanism utilized provides the strength and stability necessary to accomplish the adjustment feature without sacrificing the safety necessary for confident use of the prosthetic device by an amputee. Because the amputee, after brief training, can learn to recognize and appreciate the optimum heel height of his prosthetic device, the adjustable leg prosthesis will comprise a safer and more comfortable device than conventional systems.

The particular adjustment mechanism utilized, is located in the ankle section of the prosthetic leg, and adjustably couples a foot member to an ankle member which in turn is fixed to a shin member by conventional lamination techniques. The foot flexion angle is proximate the lower portion of the ankle member to provide a natural appearing contour to the prosthetic leg at all positions of adjustment.

These and other features will become apparent on a consideration of the detailed description of the preferred embodiments.

BRIEF DESCRIPTION OF THE DRAWINGS

FIG. 1 is a side elevational view, partially fragmented, of the adjustable prosthetic ankle assembly incorporated into a leg prosthesis.

FIG. 2 is an end elevational view, partially fragmented, of the unit of FIG. 1.

FIG. 3 is a side elevational view, partially fragmented, of an alternate embodiment of the adjustable prosthetic ankle assembly.

DETAILED DESCRIPTION OF THE PREFERRED EMBODIMENTS

Referring to FIG. 1, the adjustable ankle assembly, designated generally by the reference numeral 10, is shown installed in a leg prosthesis 12. The leg prothesis 12 comprises three principal integrated elements, a shin member 14, and ankle member 16, which in this instance comprises the overall adjustable ankle assembly, and, a foot member 18. The various members may be fabricated primarily from wood block or from a high density foam or other composition material which preferably can be contoured to simulate a natural anatomical extremity. While the embodiment shown in FIGS. 1 and 2, and in the alternate embodiment shown in FIG. 3 for the ankle assembly incorporate a wooden block, it can be appreciated that other supporting materials and compositions can be employed. Furthermore, the ankle assembly of FIG. 3 can be provided without a block and attached directly to a tubular leg or shin member.

In FIGS. 1 and 2, an ankle assembly mechanism 20 is contained largely within a contoured wooden block 22. The assembly includes a base bracket 24 seated within an alignment recess 26 in the block 22 and fastened to the block by a cap screw 28 and a complimentary locking wood nut 30 countersunk into the top of the block 22. The ankle assembly block 22 is thereupon laminated to the shin member 14 to provide a permanent rigid joinder of the ankle assembly and shin member.

The depending spaced sides 32 of the yoke-like, base bracket 24 include two cross pins 34 which pass through two eccentrically positioned clamp holes 36 through a pair of cylindrical pivot inserts 38. The pivot inserts 38 each includes a flex hole 40 and spacer channel 42 that communicate with the clamp hole 36 to permit the pivot inserts 38 to flex and clamp around the cross pins 34 when the pivot inserts are compressed on tightening of an adjustment mechanism by the user. The use of dual eccentric pivots provides the necessary stability and rigidity of the system once the assembly mechanism is adjusted and clamped.

The pivot inserts 38 are retained in clamping cylinders 39 in the rocker block 46 for select pivot about a pair of spaced horizontal pivot axes. The rocker block 46 has a base face 48 that is coupled to the top face 50 of the foot member 18 and fastened by an elongated cap screw 52 passing through the foot member and threaded into the rocker block 46.

The rocker block 46 includes clamping slots 54 communicating with the clamping cylinders 39 in the rocker block 46 to permit collar portions 56 of the rocker block 46, which substantially encompass the pivot inserts 38, to compress and lock the pivot inserts 38, when a pair of horizontal clamping screws 58 are tightened. The clamping screws 58 each have a readily accessible cap nut 60 which is operable from the front of the ankle member by a conventional Allen wrench (not shown) to provide the user with a convenient adjustment mechanism. To maintain a natural appearance and accomodate the adjustable tilt of the foot member with respect to the ankle member, a compressible contoured foam collar 62 is provided between the wooden block portion of the ankle assembly and the top of the foot member. The foam collar 62 is provided with access holes 66 at the cap nuts 60 for loosening and tightening the clamping screws.

A user can simply loosen the clamping screws 58 by partially unthreading the cap nuts 60. The loosened clamping screws 58 relax the clamping forces of the collar portions 56 of the rocker block 46 on the inserts 38, and hence, the compression forces of the pivot inserts 38 on the cross pins 34. The user can then manually and adjust the tilt of the foot member to the heel height desired or found most comfortable, and then tighten the nuts to secure the relative position of foot and leg.

Referring now to FIG. 3, an alternate embodiment of the ankle assembly is shown. The assembly mechanism 70 of FIG. 3 is essentially the same as that for FIG. 1 with the parts inverted.

The base bracket 72 is shown with a broken away bracket side 74 to reveal the rocker block 76. In this embodiment, the base bracket 72 has a bottom face 77 with locating screws 78 and bolt hole 79 for coupling to the top of a foot member (not shown), in a similar manner as the embodiment of FIG. 1. The rocker block 76 in turn is coupled to a rough cut ankle block 80 having an integral support tube 82 for easy connection to the ankle assembly mechanism. The block on fitting to a shin member is trimmed to shape for the particular user. The coupling is accomplished by an expansion nut 84 and cap screw 86 at the end of a pedestal 88 inserted into the tube 82. The pedestal 88 is fastened to the rocker block 76 by a large flat head screw 90.

The tilt adjustment is again accomplished by the arrangement of dual pivot inserts 92 and eccentric cross pins 94. The collar portion 96 of the rocker block encompassing the inserts is operationally the same as the collar portion 56 of the embodiment of FIG. 1, which latter member is more angular to maximize the area of the coupling face 48 of the rocker block 46. A pair of connecting screws 98 and nut plate 100 provide for loosening and tightening of the mechanism for adjustment activated by a single clamping screw 102 in the front.

While in the foregoing specification embodiments of the invention have been set forth in considerable detail for the purposes of making a complete disclosure of the invention, it should be apparent to those of ordinary skill in the art that numerous changes may be made in such details without departing from the spirit and principles of the invention.

What is claimed is:

1. An ankle assembly for a leg prosthesis having a prosthetic shin member and a prosthetic foot member for adjustment of the foot flexion angle comprising an adjustment mechanism having:
   a. a shin connecting member having coupling means for connecting said shin connecting member to the shin member;
   b. a foot connecting member having coupling means for connecting said foot connecting member to the foot member;
   c. pivotal interconnecting means for pivotally interconnecting said shin connecting member to said foot connecting member; and
   d. locking means for locking said shin connecting member to said foot connecting member in a select pivotal orientation of said shin connecting member relative to said foot connecting member wherein said shin connecting member comprises a base bracket with sides and a pair of spaced cross pins horizontally disposed between said sides; said foot connecting member comprises a rocker block with a pair of horizontally disposed clamping cylinders corresponding to the cross pins of said shin connecting member; said pivotal interconnecting means comprises a pair of cylindrical inserts in said clamping cylinders with eccentrically located clamping holes engageable with said cross pins which in cooperation with said clamping cylinders and said cross pins provides limited pivotal movement of said base bracket relative to said rocker block; and said locking means comprises at least one tightening screw operably engaging said clamping cylinders wherein tightening of said screw clamps and locks said cylindrical inserts and said cross pins.

2. An ankle assembly for a leg prosthesis having a prosthetic shin member and a prosthetic foot member for adjustment of the foot flexion angle comprising an adjustment mechanism having:
   a. a shin connecting member having coupling means for connecting said shin connecting member to the shin member;
   b. a foot connecting member having coupling means for connecting said foot connecting member to the foot member;
   c. pivotal interconnecting means for pivotally interconnecting said shin connecting member to said foot connecting member; and
   d. locking means for locking said shin connecting member to said foot connecting member in a select pivotal orientation of said shin connecting member relative to said foot connecting member; wherein said foot connecting member comprises a base bracket with sides and a pair of spaced cross pins horizontally disposed between said sides; said shin connecting member comprises a rocker block with a pair of horizontally disposed clamping cylinders corresponding to the cross pins of said foot connecting member; said pivotal interconnecting means comprises a pair of cylindrical inserts in said clamping cylinders with eccentrically located clamping holes engageable with said cross pins which in cooperation with said clamping cylinders and said cross pins provides limited pivotal movement of said base bracket relative to said rocker block; and said locking means comprises at least one tightening screw operably engaging said clamping cylinders wherein tightening of said screw clamps and locks said cylindrical inserts and said cross pins.

3. The ankle assembly of claims 1 or 2 wherein said coupling means of said shin connecting member comprises a block material fastened to the shin member of a composition which is bondable to the shin member and shapable to a natural appearing contour.

4. The ankle assembly of claims 1 or 2 wherein said coupling means of said shin connecting member comprises an expansion nut and bolt assembly engageable with a shin member of a type having a tube structure for rigidly connecting said ankle assembly to the skin member.

5. The ankle assembly of claims 1 or 2 wherein said coupling means of said foot connecting member comprises a bolt assembly for rigidly connecting said ankle assembly to the foot member.

6. An ankle assembly for a leg prosthesis having a prosthetic shin member and a prosthetic foot member for adjustment of the foot flexion angle comprising an adjustment mechanism having:
 a. a shin connecting member having coupling means for connecting said shin connecting member to the shin member;
 b. a foot connecting member having coupling means for connecting said foot connecting member to the foot member;
 c. pivotal interconnecting means for pivotally interconnecting said shin connecting member to said foot connecting member said pivotal interconnecting means comprising a pair of spaced eccentric pivots; and
 d. locking means for locking said shin connecting member to said foot connecting member in a select pivotal orientation of said shin connecting member relative to said foot connecting member; wherein said locking means comprises a clamping assembly, said clamping assembly having a pair of collar clamps encompassing said eccentric pivots and having an adjustable tightening means operably connected to said collar clamps for clamping said collar clamps around said eccentric pivots on select adjustment of said tightening means, wherein said shin connecting member is locked to said foot connecting member in a selected pivotal orientation.

7. The ankle assembly of claim 6 wherein said tightening means comprises at least one threaded screw engaging said collar clamps, wherein said clamps are tightened on tightening said threaded screw.

* * * * *